Figure 1:
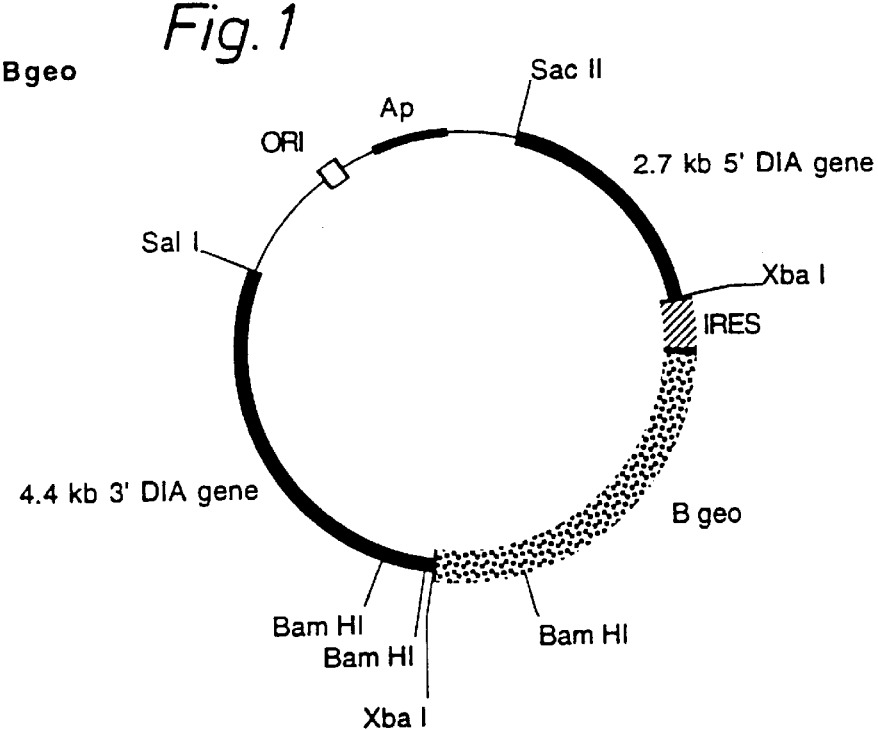
Figure 2:
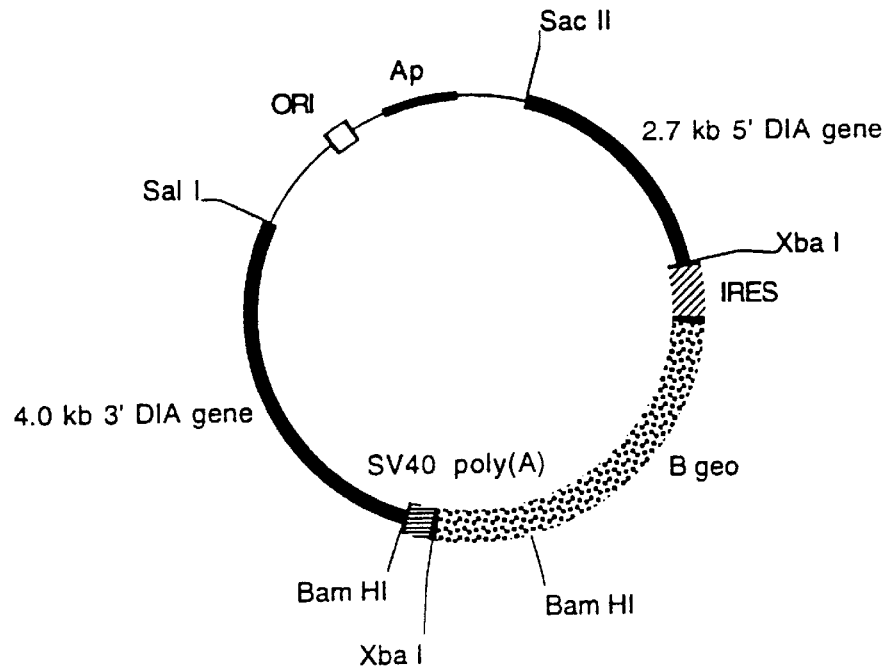

United States Patent [19]
Smith et al.

[11] Patent Number: 6,150,169
[45] Date of Patent: Nov. 21, 2000

[54] EXPRESSION OF THE HETEROLOGOUS GENES ACCORDING TO A TARGETED EXPRESSION PROFILE

[75] Inventors: Austin Gerard Smith, Edinburgh, United Kingdom; Peter Scott Mountford, Elsdernwick, Australia; Richard Frank Lathe, Edinburgh, United Kingdom

[73] Assignee: The University of Edinburgh, United Kingdom

[21] Appl. No.: 08/537,765

[22] PCT Filed: Apr. 21, 1994

[86] PCT No.: PCT/GB94/00849

§ 371 Date: Jan. 25, 1996

§ 102(e) Date: Jan. 25, 1996

[87] PCT Pub. No.: WO94/24307

PCT Pub. Date: Oct. 27, 1994

[30] Foreign Application Priority Data

| Apr. 21, 1993 | [GB] | United Kingdom | 9308271 |
| Jun. 28, 1993 | [GB] | United Kingdom | 9313323 |
| Jan. 20, 1994 | [GB] | United Kingdom | 9401011 |

[51] Int. Cl.$^7$ ................................................. C12N 15/85
[52] U.S. Cl. ........................... 435/455; 435/463; 435/352
[58] Field of Search ................................. 536/23.1, 24.1; 435/320.1, 325, 172.3, 440, 455, 463, 352

[56] References Cited

FOREIGN PATENT DOCUMENTS

WO 90/11354  10/1990  WIPO .
WO 92/20808  11/1992  WIPO .
WO 93/07266   4/1993  WIPO .

OTHER PUBLICATIONS

Chen, B.F. et al. J. Virol. vol. 67, No. 4, pp. 2142–2148, Apr. 1993.

Ali, S. et al., "Characterization of the Gene Encoding Ovine Beta–lactoglobulin: Similarity to the Genes for Retinol Binding Protein and Other Secretory Proteins", *J. Mol. Biol.* 199:415–426 (1988).

Archibald, A. L. et al., "High–level expression of biologically active human $\alpha_1$–antitrypsin in the milk of transgenic mice", *Proc. Natl. Acad. Sci. USA* 87:5178–5182 (1990).

Brinster, R. L. et al., "Introns increases transcriptional efficiency in transgenic mice", *Proc. Natl. Acad. Sci. USA* 85:836–840 (1988).

Clark, A. J. et al., "Expression of Human Anti–hemophilic Factor IX in the Milk of Transgenic Sheep", *Bio/technology* 7:487–492 (1989).

Friedrich, G. et al., "Promoter traps in embryonic stem cells: a genetic screen to identify and mutate developmental genes in mice", *Genes Devel.* 5:1513–1523 (1991).

Ghattas, I. R. et al., "The Encephalomyocarditis Virus Internal Ribosome Entry Site Allows Efficient Coexpression of Two Genes from a Recombinant Provirus in Cultured Cells and in Embryos", *Mol. Cell. Biol.* 11(12):5848–5859 (1991).

Gossler, A. et al., "Mouse Embryonic Stem Cells and Reporter Constructs to Detect Developmentally Regulated Genes", *Science* 244:463–465 (1989).

Harris, S. et al., "Complete nucleotide sequence of the genomic ovine β–lactoglobuline gene", *Nucl. Acids Res.* 16(21):10379–10380 (1988).

Heard, J.–M. et al, "Determinants of Rat Albumin Promoter Tissue Specificity Analyzed by an Improved Transient Expression System", *Mol. Cell. Biol.* 7(7):2425–2434 (1987).

Lathe, R. et al., "Plasmid and bacteriophage vectors for excision of intact inserts", *Gene* 57:193–201 (1987).

Nichols, J. et al., "Establishment of germ–line–competent embryonic stem (ES) cells using differentiation inhibiting activity", *Development* 110:1341–1348 (1990).

Okamoto, K. et al., "A Novel Octamer Binding Transcription Factor Is Differentially Expressed in Mouse Embryonic Cells", *Cell* 60:461–472 (1990).

Pelletier, J. et al., "Internal initiation of translation of eukaryotic mRNA directed by a sequence derived from poliovirus RNA", *Nature* 334:320–325 (1988).

Pilipenko, E. V. et al., "Prokaryotic–like Cis Elements in the Cap–Independent Internal Initiation of Translation on Picornavirus RNA", *Cell* 68:119–131 (Jan. 1992).

Schöler, H. R. et al., "Octamer binding proteins confer transcriptional activity in early mouse embryogenesis", *EMBO J.* 89):2551–2557 (1989).

Schöler, H. R. et al., "Oct–4: a germline–specific transcription factor mapping to the mouse t–complex", *EMBO J.* 9(7):2185–2195 (1990).

Schöler, H. R. et al., "Octomania: The POU factors in murine development", *Trends Genet.* 7(10):323–329 (1991).

Simons, J. P. et al., "Alteration of the quality of milk by expression of sheep β–lactoglobulin in transgenic mice", *Nature* 328:530–532 (1987).

Simons, J. P. et al., "Gene Transfer into Sheep", *Bio/technol.* 6:179–183 (1988).

Skarnes, W. C. et al., "A gene trap approach in mouse embryonic stem cells: the lacZ reporter is activated by splicing, reflects endogenous gene expression, and is mutagenic in mice", *Genes Develop.* 6:903–918 (Jun. 1992).

(List continued on next page.)

*Primary Examiner*—Nancy Degen
*Assistant Examiner*—Irem Yucel
*Attorney, Agent, or Firm*—Finnegan, Henderson, Farabow, Garrett & Dunner, LLP

[57] ABSTRACT

This invention relates to DNA constructs for inserting heterologous gene sequences into a host genome so as to obtain expression of the heterologous gene, to methods of inserting heterologous gene sequences into a host genome, and to organisms carrying modified host genomes. Specifically, the DNA constructs of this invention contain an expression unit of an internal ribosome binding site (IRES) coupled to a heterologous gene sequence. This expression unit is flanked at the 5' and 3' ends by DNA sequences that enable homologous recombination or integration of the construct with the DNA of a targeted host to obtain expression of the heterologous gene in the host.

29 Claims, 9 Drawing Sheets

OTHER PUBLICATIONS

Smith, A. G. et al., "Targeted Mutagenesis of the Stem Cell Specific Transcription Factor Oct–4", *J. Cell. Biochem. Suppl. 18B*:189 (Feb. 1994).

Tomasetto, C. et al., "Breast Cancer Protein PS2 Synthesis in Mammary Gland of Transgenic Mice and Secretion into Milk", *Mol. Endocrinol. 3*:1579–1584 (1989).

Ure, J. M. et al., "A rapid and efficient method for freezing and recovering clones of embryonic stem cells", *Trends Genet. 8(1)*:6 (Jan. 1992).

Whitelaw, C. B. A. et al., "Targeting expression to the mammary gland: intronic sequences can enhance the efficiency of gene expression in transgenic mice", *Transgenic Res. 1*:3–13 (1991).

Wood, C. R. et al., "An internal ribosome binding site can be used to select for homologous recombinants at an immunoglobulin heavy–chain locus", *Proc. Natl. Acad. Sci. USA 88*:8006–8010 (1991).

DICISTRONIC INITIATION OF TRANSLATION

TARGETING OPTIONS

EXPRESSION OF THE HETEROLOGOUS GENES ACCORDING TO A TARGETED EXPRESSION PROFILE

This application claims priority from International application PCT/GB94/00849, filed Apr. 21, 1994.

This invention relates to DNA constructs for inserting heterologous gene sequences into a host genome so as to obtain expression of the heterologous gene, to methods of inserting heterologous gene sequences into a host genome and to organisms carrying modified host genomes.

In one particular aspect this invention relates to constructs for inserting a heterologous gene into an endogenous gene in a host genome so that the heterologous gene is expressed in place of or in addition to the endogenous gene. In a second particular aspect this invention relates to methods for functionally integrating a heterologous gene sequence (transgene) into a specified gene of a host genome so as intimately to couple transgene expression with the endogenous transcriptional and post-transcriptional regulatory elements, to constructs for use in said methods, and to genetically modified cells and transgenic animals generated with such constructs and their descendants.

Genetic engineering involves the fusion of different gene sequences. In many cases this is performed with the intention of expressing a heterologous gene sequence in a fashion which is identical to or in part reflects the expression pattern of another gene. To achieve the desired expression level, distribution and/or timing or the sequence being expressed, regulatory sequences of the gene being copied are fused with the sequences of the gene which is to be expressed to generate an expression construct. However, in many applications involving higher eukaryotic cells, such as the selection of particular stem cells or the production of heterologous proteins from transgenic animals, it is extremely difficult to generate an expression construct whose pattern and level of expression adequately mimics those of the gene being copied.

It is known to introduce heterologous genes into mammalian cells including stem cells, transgenic animals and in vitro maintained cell lines. However, despite specific design, existing expression constructs, when integrated into the host genome, rarely provide the desired level and distribution (both spatial and temporal) of gene expression. Expression constructs are known that attempt to mimic the expression profile of an endogenous gene by incorporating known regulatory elements of the endogenous gene. However, success with these constructs is low partly because functional detail of the endogenous gene structure including the location and identity of such elements and the contribution each component makes in regulating gene expression, for the most part, remains unknown. Other problems are associated with randomly integrating expression constructs including positional effects of the site of integration and random mutation of endogenous gene expression.

Furthermore, to position and define regulatory elements in endogenous genes, often at some distance from the transcribed region of the gene, often demands much painstaking work. The distal positioning of these elements is also often important to their function and may be difficult to reproduce in transgenic expression constructs.

Further still, having identified and engineered the endogenous regulatory elements into heterologous gene expression constructs, there is little assurance that any particular transgenic expression construct will function correctly once introduced at random into the genome.

Early attempts to produce heterologous proteins in transgenic animals principally focused on the use of transgene constructs comprising promoter regions derived from one gene fused to cDNA coding sequences from another gene. For the most part the fusion constructs function poorly, if at all, and the level of expression obtained is far lower than that of the endogenous gene.

This is in contrast with intact genes, such as the ovine whey protein betalactoglobulin (BLG). High-level expression of the encoded protein is obtained in transgenic mice harbouring a full-length BLG gene complete with all introns and adequate lengths of 5' and 3' untranscribed regions (Simons et al., Nature 328,530–532, 1987).

Attempts were made by various groups to harness the efficient expression of such genomic transgenes to drive the expression of heterologous coding sequences in transgenic animals. Tandem gene constructs are not normally expressed in mammalian systems because only the first (upstream) coding sequence is translated. For this reason most workers were obliged to fuse, into the 5' untranslated region (5'UTR) of the genomic gene, a cDNA coding for the heterologous protein of interest.

Tomasetto et al. (Mol. Endocrinol. 3, 1579–1584, 1989) fused a pS2 cDNA into the 5'UTR of the whey acidic protein (WAP) gene. Although some expression was observed, the production level was extremely low. Similarly, Simons et al. (Bio/Technology 6, 179–183, 1988) produced constructs in which cDNA's encoding human factor IX or alpha-1 antitrypsin were introduced into the 5'UTR of ovine BLG. Both in transgenic mice and transgenic sheep these constructs failed to function properly, with only low levels of expression being obtained (Clark et al., Bio/Technology 7, 487–492, 1989).

Although some reports indicate that the simple insertion of intron sequences into expression constructs can augment expression (eg. Brinster et al., Proc. Natl. Acad. Sci. 85, 836–840, 1988) the level of expression remains low compared with that of the endogenous gene, suggesting that intron sequences per se are not sufficient to permit high-level gene expression in a transgenic context. This is confirmed by the results of Whitelaw et al. (Transgenic Res. 1, 3–13, 1991) who deleted the introns from the BLG gene and then added back a single intron. The intron-less gene was poorly active and the presence of a single intron was not sufficient to restore the transcriptional efficiency of the BLG gene in transgenic mice.

It has been argued that the overall gene structure, including the relative positions of introns and exons, is critically important for transgene function. This contention is wholly supported by the finding that the 5' end of the BLG gene, when fused to a genomic copy of the human alpha-1 antitrypsin gene, leads to consistent high-level expression in transgenic animals (Archibald et al., Proc. Natl. Acad. Sci. U.S.A. 87, 5178–5182, 1990).

In practice, however, it is often difficult to apply this genomic fusion technology. Many genes of particular interest are extremely large (eg. the human factor VIII gene is over 100 kilobases in length) and the generation of fusion constructs, and their introduction into transgenic mammals (including livestock) is extremely difficult.

An alternative to engineering expression constructs (by coupling regulatory elements of one or several gene/s with the heterologous gene sequence to be expressed) in vitro, is to utilise the "gene trap" approach. Regulatory elements controlling expression of gene trap expression constructs, are provided by inserting the heterologous sequence which is to be expressed, into a gene in the host's genome. Sequences of the gene to be expressed are thereby intimately coupled with the regulatory elements of the endogenous gene.

By far the great majority of gene trap type vectors are used for random integration or trapping of host genes, with the disadvantage that there is no control over the site of integration or the generation of endogenous gene/transgene fusion products. One gene trap vector, pGT4.5 is known from Genes & Development 6:903–918 by Cold Spring Harbour Laboratory Press, 1992.

A major limitation in the design and functional utilisation of all "gene trap" and "genomic transgene" expression constructs known in the prior art, is the mechanism of transgene translation initiation. Translation of most mRNAs is initiated by a scanning mechanism in which a ribosome complex (termed 43S) binds at the 5' end of capped mRNA and moves along the mRNA until a suitably placed AUG initiation codon is detected. Subsequently a second ribosome subunit (termed 60S) joins the complex and protein synthesis begins.

In 1988, Pettetier and Sonenberg (Nature, 334:320–325) showed that some picornavirus mRNAs are translated by an unusual mechanism of "internal ribosome binding" and that these particular mRNAs contained specific sequences internal to the mRNA that enabled a ribosome to bind and initiate translation. The sequences were termed "Internal Ribosome Entry Site" (IRES). Picornaviruses infect human cells so this work indicated that eukaryotic ribosomes recognised the IRES and could initiate translation internally, and other than via a cap-dependent mechanism.

Ghattas et al (Molecular & Cellular Biology, Vol. 11 No. 12, December 1991, pp5848–5859) describe the use of an internal ribosome entry site in obtaining co-expression of two genes from a recombinant provirus in cultured cells and in chicken embryos.

However, there currently exists no efficient procedure by which a heterologous gene sequence (transgene) to be expressed in eukaryotic cells, in particular mammalian stem cells, transgenic animals or cultured cells, can be inserted into the genome of a host cell so as to obtain expression of that heterologous gene in a desired pattern, one example of a desired pattern being intimately to couple expression of the heterologous gene with regulatory elements controlling expression of a targeted endogenous gene.

It is an object of the invention to provide a DNA construct and methods for its use that enable improved efficiency of heterologous gene expression in a host cell. To provide the heterologous gene expression at a desired level is another object. A further object is to provide expression with a desired temporal and/or spatial profile during the life of a host cell or population of cells or transgenic organism.

By "heterologous gene expression" is meant both (1) expression in a host of a gene that was previously not expressed in that host, and (2) expression in a host of a gene according to a particular expression profile, the gene being previously expressed in the host but not according to the particular expression profile.

Accordingly, in a first aspect the invention provides a DNA construct for inserting a heterologous gene sequence into a host genome, the construct comprising the following sequence:

5'X-A-P-B-Q-C-Y3' in which

X and Y are, separately, DNA sequences substantially homologous with a host gene locus, P is an internal ribosome entry site (IRES), Q is the heterologous gene sequence, and A, B and C are optional linker sequences.

X and Y should be of sufficient length and homology with host sequences to enable homologous recombination to take place between the DNA construct of the invention and the corresponding host genome DNA. It is preferable that X and Y are each at least 1000 base pairs. However, it will be appreciated that, in general, while effective homologous recombination is in some instances achieved with X and Y having rather short sequences, efficiency will be increased as the length of the sequences increases. X and Y are preferably at least 95% more preferably at least 98%, and most preferably substantially 100% homologous with the host.

In embodiments of the invention, X and Y (i) together constitute a DNA sequence substantially homologous with a single continuous host DNA sequence or (ii) are substantially homologous with two separate sequences from the same endogenous host gene locus and in the same respective orientation as in the endogenous locus. In a preferred embodiment, the DNA construct is part of a vector capable of transforming a host cell by inserting the DNA construct into the host cell DNA.

P, the IRES, is 5' to the open reading frame of the heterologous gene sequence Q. Where B is absent, the IRES is immediately 5' to the open reading frame of the heterologous gene.

The linker regions A, B and C are additional DNA sequences optionally present in the DNA construct. The linker regions may be inserted into the construct or may arise as a result of the recombinant DNA techniques used in making the construct. In an embodiment of the invention linker region A includes or consists of a splice acceptor. The size and nature of linker B in particular is important in providing an optimal linkage between the IRES and the heterologous gene (Cell, Vol.68, pp119–131, January 1992).

To select for successful transformants expressing the heterologous gene it is convenient to include a selectable marker, for example an antibiotic resistance gene or a hypoxanthine ribosyl transferase gene, in the heterologous gene. Including a selectable marker enhances the probability of selecting transfected cells with the desired transgene integration as expression of the selectable marker is dependent upon functional integration into an active gene. Transgene integrations in non-transcribed regions of the genome are therefore readily eliminated.

When a construct according to the invention is used to transform a host genome, homologous recombination with the host DNA results in insertion of the construct into a host gene. Transcription of the heterologous gene is then under control of the regulatory elements associated with the host gene. Translation of the heterologous gene coding sequence is then enabled by the presence of the IRES 5' to the open reading frame of the heterologous gene. This results in regulated expression of the heterologous gene with considerably greater efficiency than under hitherto known and used techniques for obtaining heterologous gene expression.

In use, a heterologous gene and an endogenous gene with a particular pattern and/or level of expression in a host cell are selected. A DNA construct is made having X and Y substantially homologous to parts of the endogenous gene or to flanking regions of the endogenous gene. The DNA construct will then target insertion of the heterologous gene plus IRES into (or in place of) that endogenous gene so that heterologous gene transcription is directed by the host regulatory elements for that endogenous gene. Translation of mature heterologous gene product is enabled by the IRES included in the DNA construct and newly inserted along with the heterologous gene.

The utilisation of IRES-mediated translation initiation in gene trap type targeting vectors according to the invention provides a considerable advantage over previously described gene traps and gene trap targeting vectors in that functional integration of the transgene into the desired endogenous gene transcribed region does not produce a fusion protein and need not necessarily disrupt endogenous gene expression.

Octamer binding transcription factor 4 is a member of the POU family of transcription factors (reviewed by Schöler, 1991). Oct4 transcription is activated between the 4- and 8-cell stage in the developing mouse embryo and it is highly expressed in the expanding blastocyst and then in the pluripotent cells of the inner cell mass. Transcription is down-regulated as the primitive ectoderm differentiates to form mesoderm (Schöler et al., 1990) and by 8.5 d.p.c. (days post coitum) is restricted to migrating primordial germ cells. High level Oct4 gene expression is also observed in pluripotent embryo carcinoma and embryonic stem cell lines, and is down-regulated when these cells are induced to differentiate (Schöler et al., 1989; Okamoto et al., 1990).

The Oct4 gene was selected as a suitable example of the use of the constructs of the invention because of the known moderate to high levels of Oct4 mRNA. Results show that despite a down-regulation in transcription from the targeted Oct4 allele, consistent with the removal of a possible enhancer sequence in the second intron, the Oct4 gene can be targeted at very high efficiency using the methods and constructs of the invention.

In one embodiment of the invention integration of a transgenic construct incorporating an IRES element and an open reading frame into a position 3' to the stop codon and 5' of the polyadenylation signal generates a functional dicistronic mRNA capable of encoding both the endogenous gene product and the product of the transgenic open reading frame. In another embodiment transgene integration 5' to or in place of the endogenous gene reading frame provides an opportunity to "knock-out" (or otherwise modify) the endogenous gene product.

Analyses of eukaryotic genes in many laboratories have shown that in general the coding sequences of DNA, the regions that will ultimately be translated into amino acid sequences, are not continuous but are interrupted by 'silent' DNA. Even for genes with no protein product, such as tRNA genes of yeast in Drosophila, the primary RNA transcript contains internal regions that are excised during maturation, the final tRNA or mRNA being a spliced product. The regions which will be lost from the mature messenger are termed "introns" (for intragenic regions) and alternate with regions which will be expressed, termed "exons". Transgenes may be functionally inserted into exons, or in a further aspect of the invention, incorporate a splice acceptor sequence 5' to the IRES element to enable functional integration into an intron. Functional transgene integration is therefore not restricted by the intron/exon arrangement or reading frame of the endogenous gene. This is another aspect in which the design and construction of transgenic constructs of the invention is simpler than that of hitherto known constructs.

The IRES containing vectors of the invention enable gene targetting with increased efficiency. The invention permits a heterologous gene coding sequence to be inserted into the 3' untranslated region of a gene (3'UTR), therefore conserving the relative positions of all the upstream introns and exons, and leading to high-level expression. The requirement for a genomic copy of the heterologous gene is avoided, and successful expression can be obtained by inserting a cDNA copy downstream of the IRES in the 3'UTR. Because cDNAs are very much shorter that the corresponding genomic copy, the assembly of constructs and the generation of transgenic mammals is considerably facilitated.

In a preferred embodiment the heterologous gene includes at its 3' (downstream) end a polyadenylation signal. An advantage of this embodiment is that the polyadenylation signal results in efficient truncation and processing of the transcript at the end of the heterologous gene.

In particularly preferred embodiments the DNA construct also includes a truncation/cleavage/transcription termination sequence 5' (upstream) of the homologous region X. The function of the 5' sequence is to prevent mRNA readthrough; suitable sequences include a poly A signal, such as the SV40 polyadenylation signal, and the Upstream Mouse Sequence (UMS) (Heard et al., 1987). The 5' sequence can further include a splice acceptor. It is known that DNA constructs can integrate at random into the host genome, i.e. that they do not always insert by homologous recombination with the targeted endogenous gene. Random integration into any active gene can result in heterologous gene expression; this makes it difficult to recognize correct insertion events, which is a disadvantage. The particularly preferred embodiments overcome this problem because where random integration occurs the transcription termination or truncation or cleavage sequence also integrates, blocking transcription. It is advantageously found that where homologous recombination occurs with the targeted endogenous gene, the transcription blocking sequence does not integrate, so transcription of the heterologous gene is possible.

In these particularly preferred embodiments of the invention are established methods effectively to eliminate expression after random gene trap integration events and thereby provide a gene trap type targeting strategy which enables selection specifically for the desired targeting event. This method is termed by the inventors Positive Only Selection (POS) and utilises transcript truncation/cleavage sequences (e.g. polyadenylation sequences) or transcriptional termination sequences such as the UMS, to block expression of the transgene in the event of random integration into actively transcribed genes. Homologous recombination with the target gene functionally inserts the heterologous gene and, if present, a selectable marker, but not the upstream transcriptional termination sequence, and therefore permits transcription of the heterologous gene and, where present, the selectable marker.

Thus "POS" embodiments of the invention extend the potential of the gene trap expression technology by providing methods of essentially eliminating expression of the transgene from sites of integration other than the desired target gene. The POS system has particular application in gene therapy where restricting transgene expression to the targeted locus would be of enormous value.

Using the DNA constructs of the first aspect it is possible to insert a heterologous gene into an endogenous host gene so that the start of the heterologous gene sequence is inserted substantially at the start of the endogenous target gene sequence. In such cases the IRES is optionally omitted, i.e. the DNA construct comprises:

5'T-D-X-A-Q-C-Y3' wherein

T is a transcription terminator or truncator,

D is an optional linker sequence, and

X, Y, A, C and Q are as previously defined.

The constructs of the invention are also advantageous for addressing the problem of expressing in a target host cell or organism (which we designate for clarity as cell "T") a gene ("G") according to particular expression profile ("E") where endogenous genes with a suitable expression profile are not present or are not accessible. The solution is to identify a donor host cell ("D") that includes a gene ("H") with expression profile E and to create a construct according to the invention in which X and Y are of such length that they include the cell D elements that regulate expression of the endogenous gene in cell D according to profile E. The DNA construct thus includes (1) the cell D regulatory elements for a targeted endogenous gene, the expression profile E of which is desired to be mimicked, (2) an IRES and (3) a heterologous gene sequence G. The DNA construct is allowed randomly to integrate into the cell T DNA.

Random integration of the construct into the cell T DNA generates a modified cell T expressing the heterologous gene according approximately to expression profile E of cell D. The result is expression of the gene in cell T with a similar pattern to that of H in cell D.

Following random integration of the DNA construct of the invention into cell T, the modified cell T is target for DNA constructs according to any embodiment of the invention operating via homologous recombination.

In a second aspect the invention provides a method of inserting a heterologous gene into a target endogenous gene in a host cell genome comprising transforming a host cell with a DNA construct according to the first aspect of the invention. Transformation can include introducing the DNA of the invention into a cell or preparation of cells by transfection, by injection ballistics, by plasmid or viral vector or by electroporation or by fusion.

In a third aspect the invention provides a method of expressing a heterologous gene in a host cell by making a DNA construct according to the first aspect of the invention comprising the heterologous gene, allowing the DNA construct to undergo homologous recombination with the host genome and growing a culture of host cells expressing the heterologous gene.

The invention thus provides a method of using promoterless transgenic constructs flanked by regions of gene homology, such that homologous recombination between DNA of a transgenic construct and the target gene locus leads to functional insertion of the transgene into the chosen transcription unit. Transcription of the transgene is regulated by elements associated with the endogenous gene, and/or additional elements introduced to the site with the transgene. Translation of the transgenic reading frame or frames is mediated via cap-independent translation initiation through the incorporation of an internal ribosome entry site/s (IRES) immediately 5' to the open reading frame/s. This provides an exquisite level of transgene regulation and avoids many of the problems associated with the design and successful utilisation of previously described expression constructs for transgene expression.

In a fourth aspect the invention provides a method of expressing a heterologous gene in a host cell by making a promoterless DNA construct according to the invention, allowing it to undergo random integration with the host genome and growing a culture of cells expressing the heterologous gene.

In a fifth aspect the invention provides a method of expressing a heterologous gene in a host cell by engineering a functional expression construct prior to introducing the construct into the host genome. In an embodiment one such "genomic transgene" is engineered in vitro by inserting an IRES coupled to a heterologous gene which is to be expressed, into a large genomic sequence (for example a cosmid or an artificial chromosome encompassing the gene which is to be copied) which incorporates most if not all regulatory elements of the gene. In another embodiment, a genomic transgene is engineered in vitro by targeting IRES and heterologous gene which is to be expressed, into the endogenous host gene and subsequently isolating from the targeted cell line a large genomic fragment (for example, cosmid or artificial chromosome) which incorporates the IRES and sequence to be expressed and most if not all of the regulatory elements associated with the targeted gene. Large genomic transgenes then provide the desired transgene expression following random introduction into the host cell.

In a sixth aspect the invention provides a transgenic cell or transgenic organism or transgenic animal into the genome of which a heterologous gene has been inserted using a DNA construct according to the invention either by homologous recombination or by random integration. In a seventh aspect the invention provides descendants of the sixth aspect that have inherited the heterologous genes. The invention is applicable to heterologous gene expression in both eukaryotes and prokaryotes, though preferably eukaryotes and more preferably animal cells; and mammalian cells in particular.

Obviously the utility of the constructs and methods of the invention in selecting for the desired integration event is limited to introducing transgenic constructs which incorporate a selectable marker gene into endogenous genes which are expressed at sufficient levels in the cells being transfected. To introduce a non-selectable gene into an actively transcribed gene for expression independently of a selectable marker, the target locus would first be "marked" with a construct according to the invention expressing a selectable marker which can be both selected for (primary targeting) and selected against (secondary targeting). Once marked through a primary targeting event, transgene integrations into the "marked" gene could be selected for by the absence of the primary targeting gene selectable marker. This type of approach is particularly applicable where repetitive targeting of a particular gene is envisaged such as in the development of cell lines or transgenic animals for the over-expression of heterologous genes.

If the gene being targeted is not sufficiently expressed for primary gene trap "marking", promoter mediated expression of a selectable marker may be similarly employed in standard non-gene trap type targeting vectors to mark the target gene.

In a particularly preferred embodiment of the invention vectors have been constructed which employ encephalomyocarditus virus (EMCV) IRES-mediated translation of a LacZ/bacterial neomycin resistance fusion gene (βgeo, Freidrich and Soriano, 1991) for gene targeting in murine embryonic stem (ES) cells. Translation of the βgeo fusion gene generates a bifunctional gene product which provides both reporter and selectable marker gene activity. Vectors were designed to target and subsequently report (a) normal Differentiation Inhibiting Activity/Leukaemia Inhibitory Activity (DIA/LIF) gene expression by non-disruptive insertion of the transgene 3' to the endogenous gene reading frame, and (b) altered DIA gene expression resulting from a defined modification at the DIA locus, an (c) altered ocamer-binding transcription factor 4 (Oct4) expression resulting from a defined modification at the locus.

DIA is a pleiotropic cytokine which suppresses differentiation of ES cells in vitro and has been implicated in a variety of developmental and physiological processes in vivo. The DIA gene was selected as a suitable example of the use of constructs of the invention because of the known low levels of DIA mRNA. Results show that despite low steady state DIA mRNA levels (<10 copies/cell) the DIA gene can be targeted at high efficiency.

These results suggest therefore, that the use of constructs according to the invention is applicable at least in ES cells to genes expressed even at low levels.

To investigate whether IRES-mediated translation efficiency is cell type dependent, we generated a random gene trap vector according to the invention which utilises the EMCV-IRES to initiate translation of the βgeo fusion gene. Neomycin resistant cell lines which display LacZ staining in a variety of differentiated cell types were selected for blastocyst injection and the subsequent generation of chimaeras. Chimaeras were bred to provide fully transgenic animals for analysis of LacZ expression profile. This analysis should provide valuable insight into the efficiency of IRES-mediated translation in other cell types.

Figure 3:
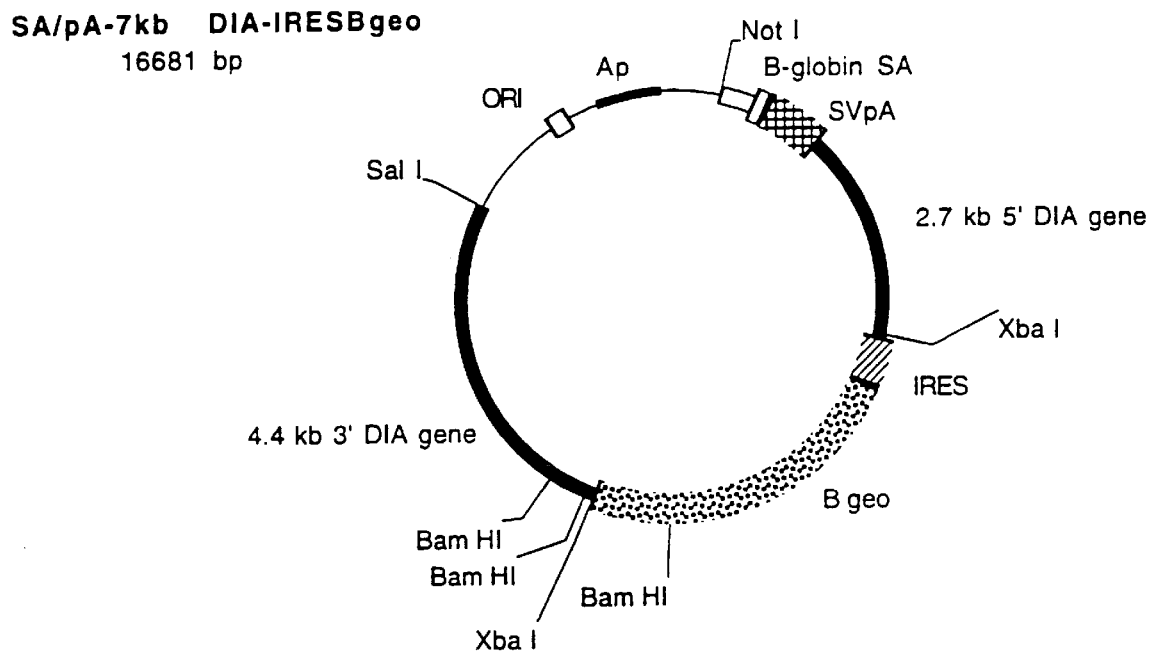
Figure 4:
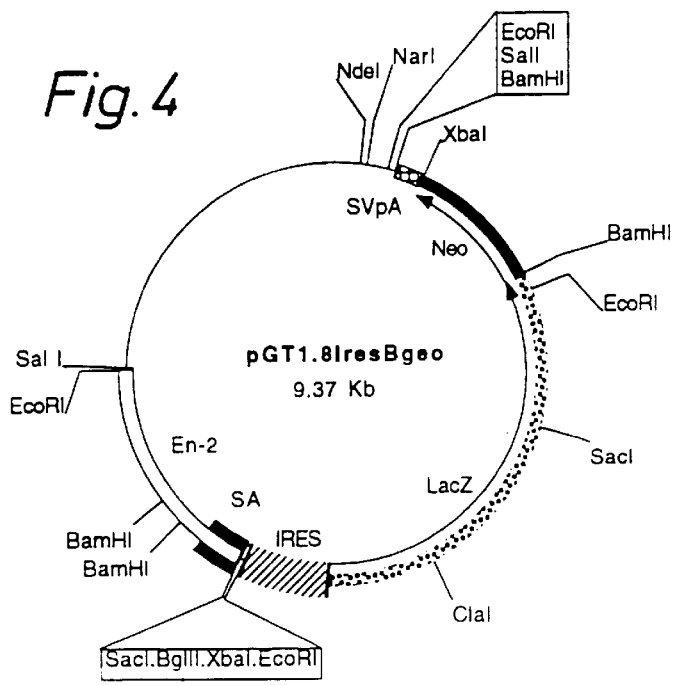
Figure 5:
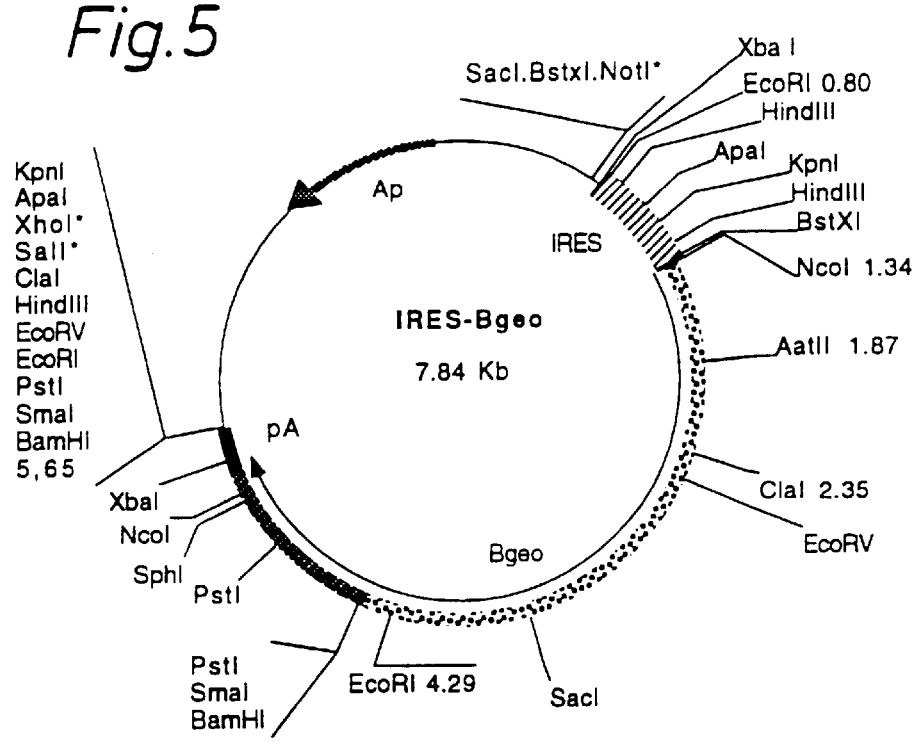

There now follow descriptions of exemplary embodiments of the invention in which FIGS. 1–3 and 6 illustrate DNA constructs of the invention, FIGS. 4 and 5 show DNA constructs for use in making the constructs.

Figure 7:
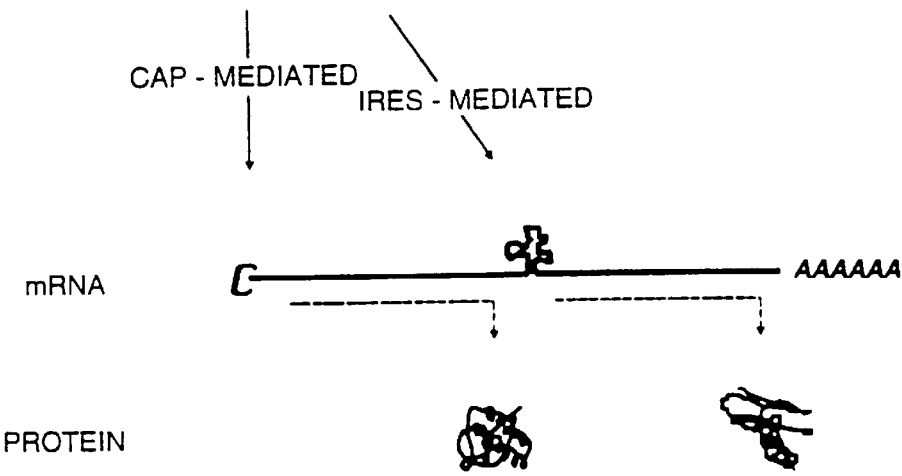
Figure 8:
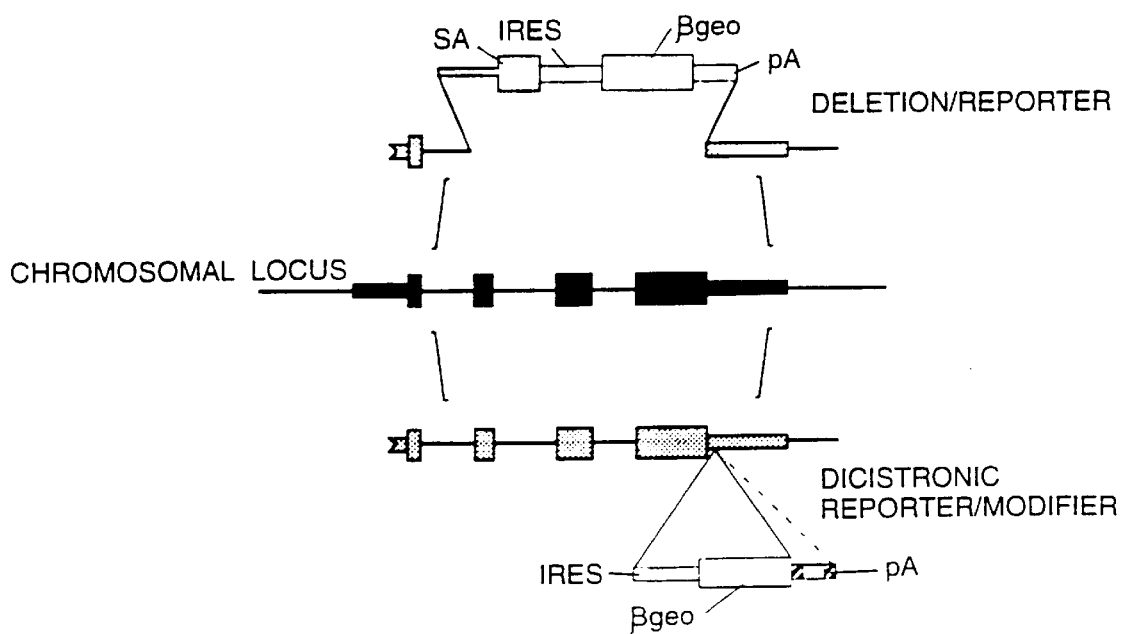

FIGS. 7 and 8 show the IRES-βgeo Targeting Strategy:

FIG. 7—Schematic representation of internal initiation of translation mediated through the IRES in a dicistronic transcript.

Figure 9:
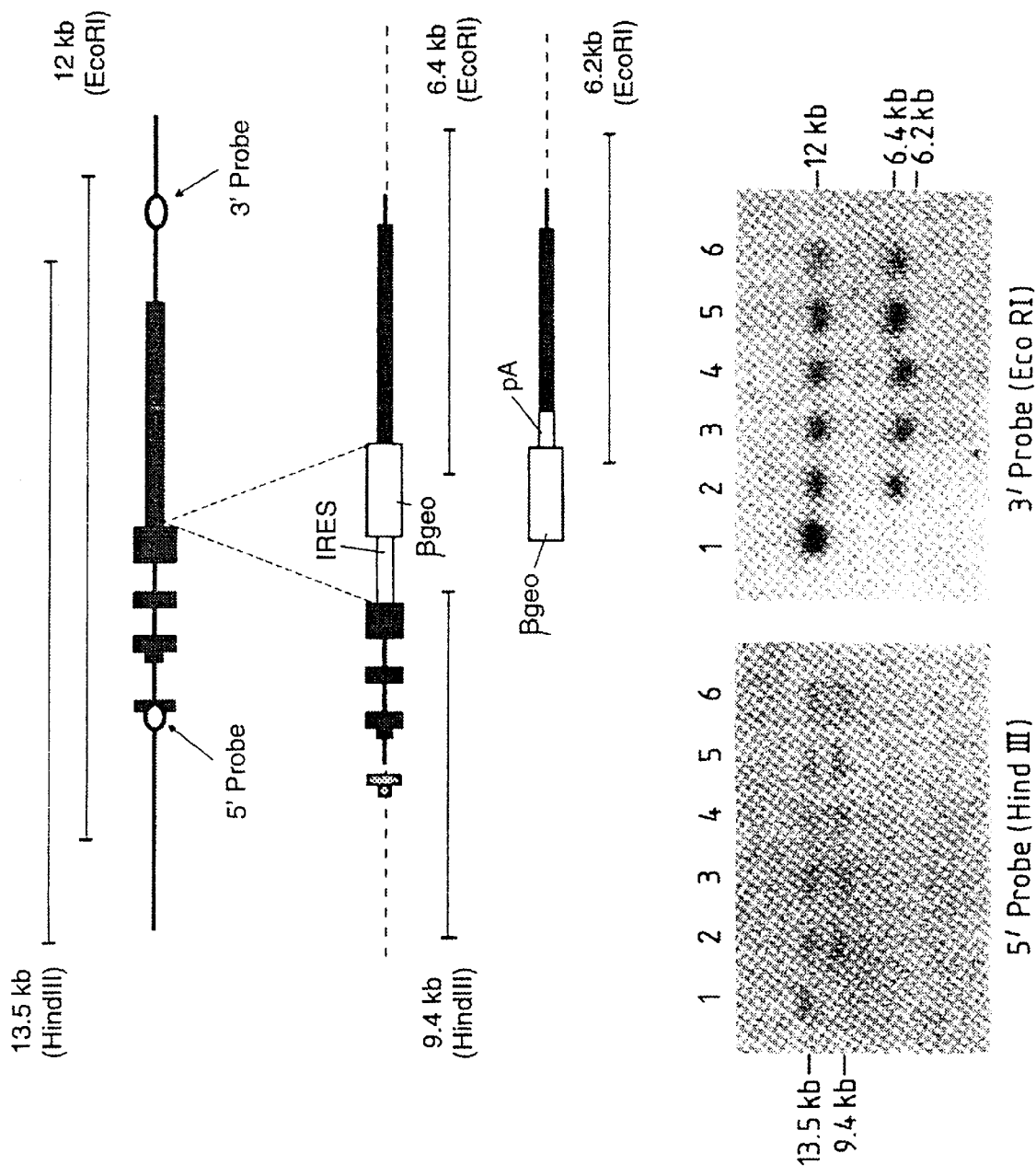

FIG. 8—applications of the IRES-βgeo cassette in gene targeting. Constructs can be designed either to delete all or part of a gene whilst incorporating the lacZ reporter, or to append the reporter with or without modification of the intact gene, and FIGS. 9–12 show DNA and mRNA Hybridisation Analyses of Targetted Clones:

FIG. 9—DIA/LIF targeting. Genomic DNA digested with Hind III or Eco RI was hybridized with either an exon 1-specific 163 bp Xho I-Eae I fragment from pDR100 or with a 700 bp Pst I-Eco RI 3' genomic fragment respectively. Lane 1, CGR8 parental ES cells; lanes 2, 5 and 6, clones targetted with the non-truncating construct; lanes 3 and 4, clones targetted with the truncating construct.

Figure 10:
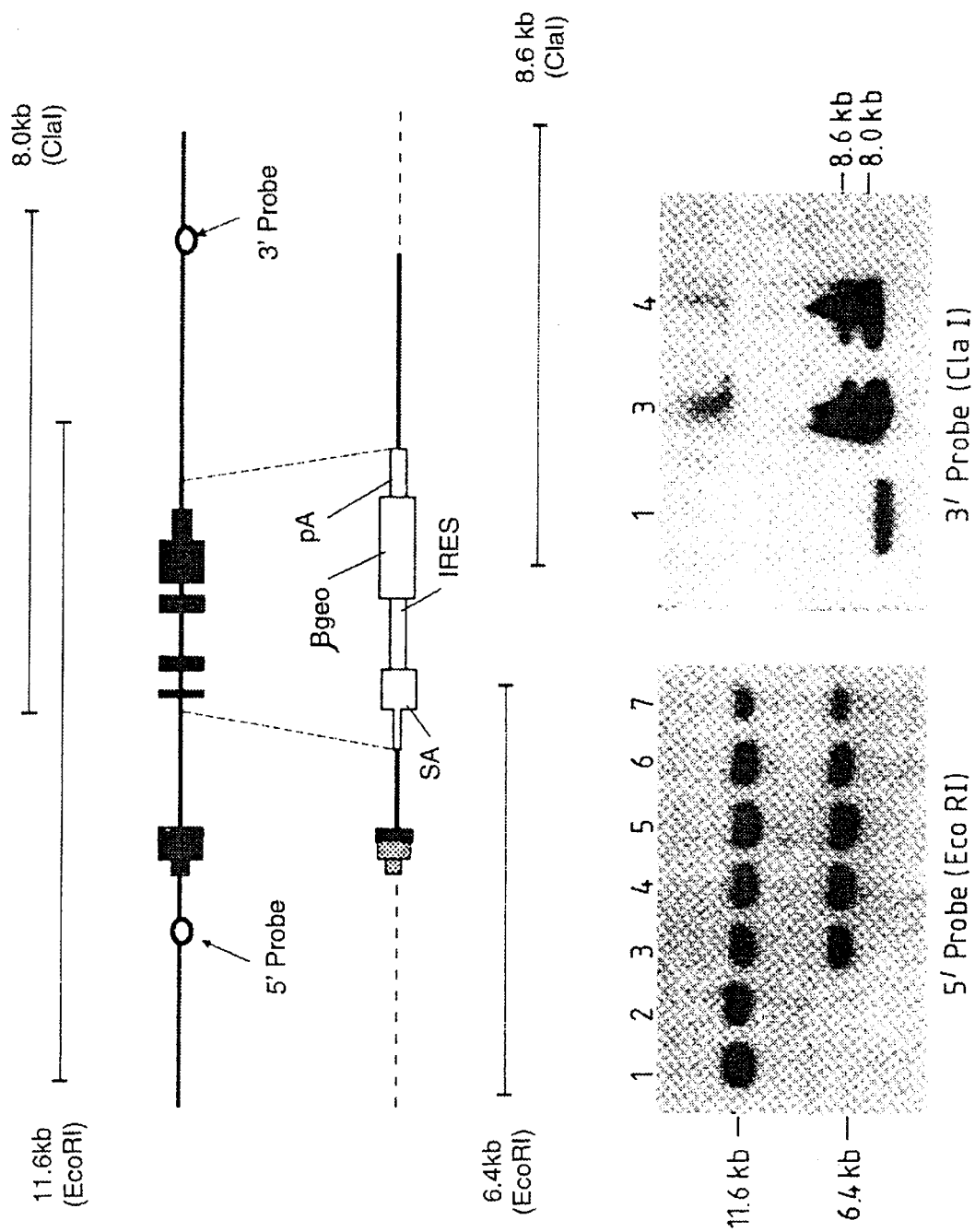

FIG. 10—Oct-4 targeting. Primary screen on genomic DNA prepared in agarose plugs by Eco RI digestion and hybridisation with a 5' 587 bp Nco I fragment, and confirmatory hybridisation with a 600 bp Hind III-Sau 3A 3' fragment following Cla I digestion of phenol/chloroform-extracted DNA. Cla I reproducibly gave partial digestion of the introduced site, suggestive of variable methylation within the lacZ sequence. Lane 1, parental CGR8 ES cells; lane 2, non-targetted transfectant; lanes 3–7, targetted clones.

Figure 11:
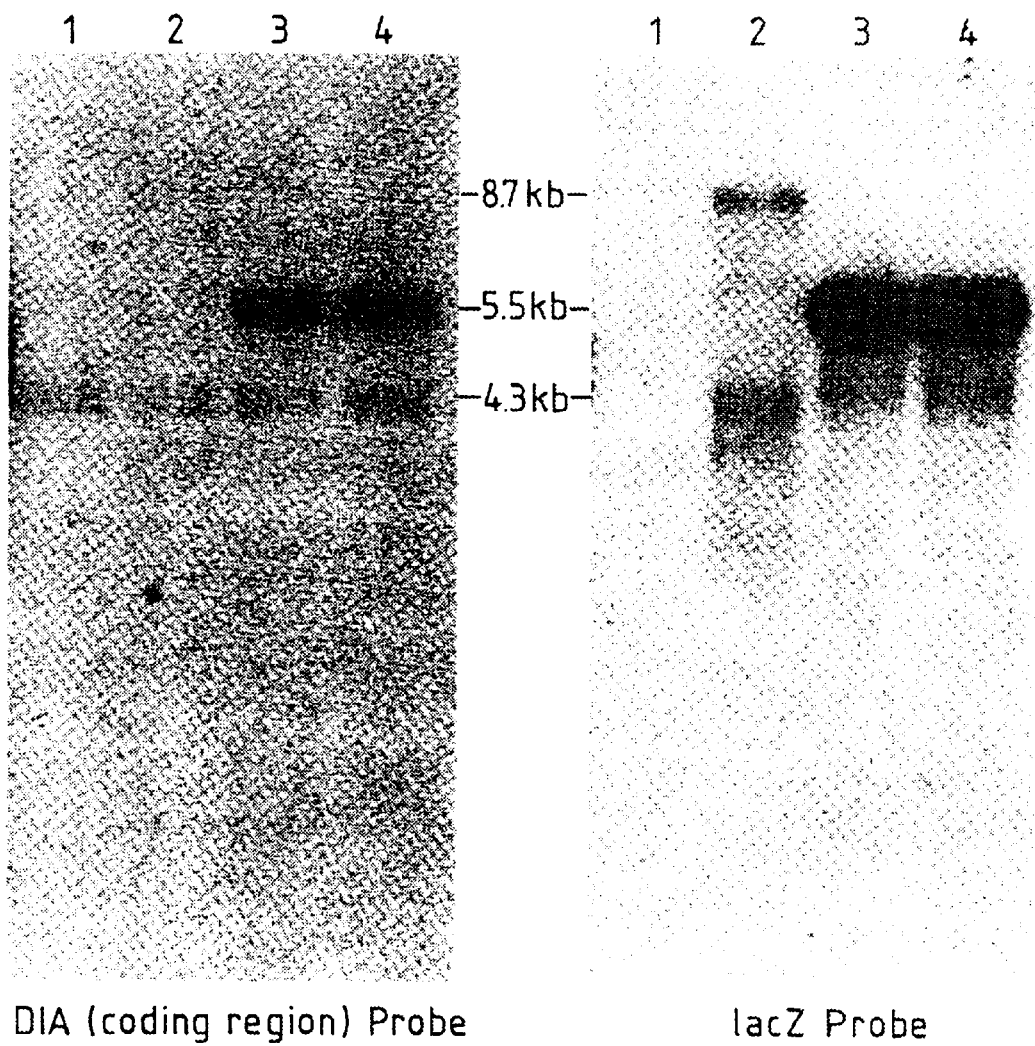

FIG. 11 Detection of fusion transcripts in ES cell clones with targetted integrations at the DIA locus. In order to increase the level of DIA expression, ES cells were induced to differentiate by exposure to $10^{-6}$M retinoic acid. Poly(A$^+$) enriched RNA was prepared after 4 days, applied to a formaldehyde gel and transferred to nylon membrane. The filter was hybridized with a 650 bp DIA/LIF coding sequence probe and exposed for 21 days, then stripped and rehybridised with an 800 bp lacZ fragment. Lane 1, RNA (1.5 μg) from parental CGR8 cells; lane 2, RNA (3 μg) from cells targetted with the non-truncating construct; lanes 3 and 4, RNA (3 μg) from cells targetted with the truncating construct.

Figure 12:
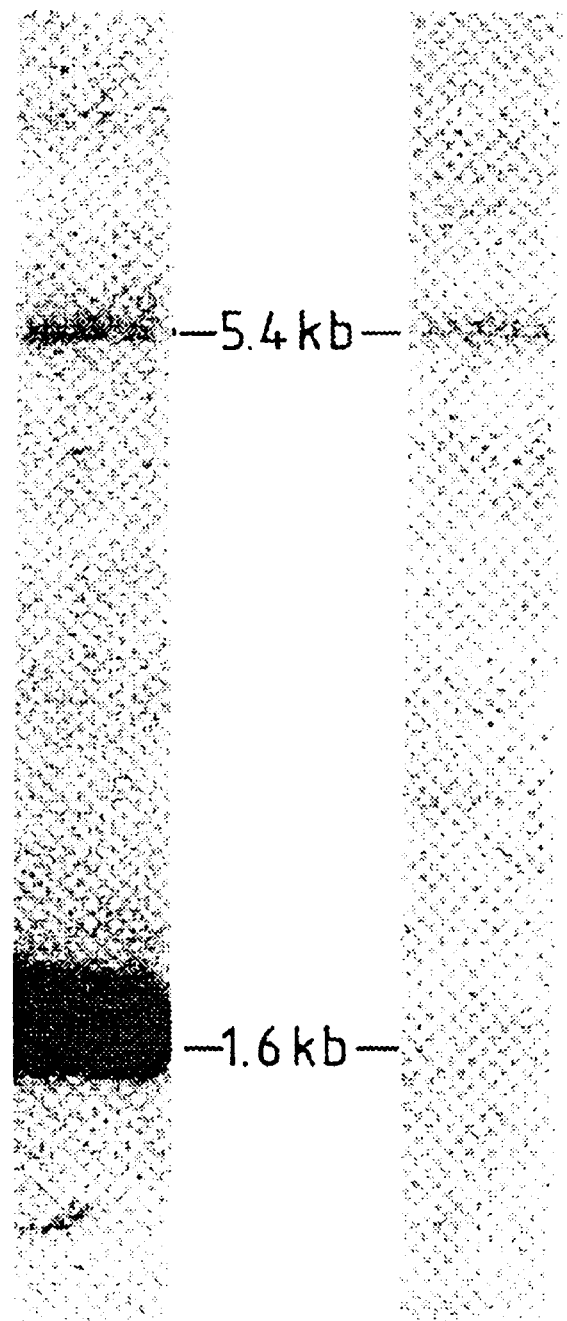

FIG. 12—Detection of fusion transcript in Oct-4 targetted ES cells. Total RNA was prepared from undifferentiated ES cells. The Oct-4 probe was a 408 bp Nco I-Pst I 5' cDNA fragment (292) which contains only 24 bp of exon 2 and should therefore give equivalent hybridisation to wild-type and fusion transcripts.

FIGS. 13A–13E show steps in the generation of a construct of the invention as described in Example 3.

EXAMPLE 1

DIA gene targeting constructs (FIGS. 1 and 2) were designed to integrate transgenes which express the β-geo fusion gene product so as to provide gene expression under the control of the endogenous DIA gene locus. A third construct (FIG. 3) was designed to demonstrate the advantages gained through transcriptional blockers which, when engineered into gene trap targeting constructs at a position 5' to the DNA targeting homology, greatly reduce if not eliminate expression from randomly integrated transgenes.

ES Cell Culture and Manipulation

ES cells were routinely maintained as described (by Smith, A. G. (1991) *J. Tiss. Cult. Meth.* 13, 89–94) in the absence of feeders in medium supplemented with murine DIA/LIF. The germline competent cell line CGR8 was established from strain 129 embryos by published procedures (Nichols, J., Evans, E. P. & Smith, A. G. (1990) *Development* 110, 1341–1348). Aggregation chimaeras were produced between ES cells and outbred MF1 embryos by a modification of the method of Wood et al. (Wood, S. A., Pascoe, W. S., Schmidt, C., Kemler, R., Evans, M. J. & Allen, N. D. (1993) *Proc. Natl. Acad. Sci. USA* 90, 4582–4585) in which co-culture is performed in hanging drops. For germ-line transmission, chimaeras were produced by blastocyst injection. For isolation of homologous recombinants, $10^8$ cells were electroporated with 150 μg linearised plasmid at 0.8 kV and 3 μFd in a 0.4 cm cuvette, then selected in the presence of 175 μg/ml G418. Genomic DNA was prepared in agarose plugs (Brown, W. R. A. (1988) *EMBO J.* 7, 2377–2385) from 24-well plate cultures while duplicate plates were stored frozen (Ure, J., Fiering, S. & Smith, A. G. (1992) *Trends. Genet.* 8, 6). To assay DIA/LIF production, ES cells were induced to differentiate by incubation with 6 mM 3-methoxybenzamide and conditioned media was harvested and assayed for the ability to inhibit ES cell differentiation as described. The assay was rendered specific for DIA/LIF by inclusion of a neutralising polyclonal antisera raised against murine DIA/LIF (AS, unpublished). Histochemical staining for β-galactosidase was carried out using X-gal (Beddington, R. S. P., Morgenstern, J., Land, H. & Hogan, A. (1989) *Development* 106, 37–46) and fluorescent staining was performed with DetectaGene Green (Molecular Probes) according to the manufacturer's instructions.

Plasmid Construction

DNA manipulations were carried out following standard procedures. The IRES is a 594 bp sequence from the 5' untranslated region (UTR) of EMCV mRNA which has been modified by mutagenesis of the native initiation codon. Translation is initiated by an ATG which lies 9 bp 3' of the normal start site and forms part of the Nco I cloning site.

Briefly, the IRESβgeo cassette was constructed by ligating a 5' fragment of the EMCV-IRES/lacZ fusion (Ghattas et al., 1991) to 3' lacZ/neo$^R$ sequences of the βgeo gene fusion (Friedrich, G. & Soriano, P. (1991) *Genes Dev.* 5, 1513–1523). The pGTIRESβgeopA plasmid was then generated by 5' ligation of the en-2 splice acceptor (Gossler, A., Joyner, A. L., Rossant, J. & Skarnes, W. C. (1989) *Science* 244, 463–465) and 3' ligation of SV40 polyadenylation sequences. Targeting constructs were prepared from genomic clones isolated from a strain 129 λ library. DIA/LIF targeting constructs were generated within a 7 kb fragment extending from a Sac II site between the alternative first exons to a Hind III site 3' of the gene. The DIA-βgeo construction was prepared by insertion of the IRESβgeo cassette into the unique Xba I site. To generate the DIA-βgeopA construct, a 1.2 kb Bam HI fragment containing 3' βgeo sequences and SV40 polyadenylation sequences was isolated from pGTIRESβgeopA and ligated into the Bam HI digested DIA-βgeo construct. This results in insertion of the 200 bp SV40 sequences in place of a 400 bp fragment of DIA/LIF 3' UTR. The Oct-4 targeting construct contained 1.6 kb of 5' homology, extending from a Hind III site within the first exon to an Xho I site in the first intron, and 4.3 kb of 3' homology extending from the Nar I site 3' of the polyadenylation sequence to a Hind III site.

In detail, to generate the DIA targeting constructs a preliminary vector coupling the EMCV-IRES to the βgeo fusion gene was engineered. This was generated by ligating a 1.2 kb Bam HI fragment encompassing the bacterial Neomycin resistance gene (neo) and the SV40 polyadenylation signal into the Bam HI site of the Bluescript II KS(−) cloning vector (Stratagene) to generate vector "1". Independently, a 1.4 kb Bgl II/Cla I fragment encompassing the EMCV-IRES and 5' LacZ sequences was isolated from pLZIN (Ghattas et al., 1991) and ligated into pGT1.8βgeo to generate the vector designated pGT1.8IRESβgeo (FIG. 4). A 4.9 kb Xba I fragment encompassing the entire IRESβgeo fusion gene was isolated from pGT1.8IRESβgeo and ligated into Xba I digested vector "1" to generate IRES-βgeo (for targeting) (FIG. 5).

To generate the DIA-IRESβgeo targeting vector (FIG. 1) the 4.9 kb Xba I IRES-βgeo fragment from IRES-βgeo (for targeting) (FIG. 5) was ligated into a unique Xba I site overlapping the translational stop codon of the murine DIA gene. The murine DIA gene fragment used in the design of the DIA gene trap targeting vectors spanned from a Sac II site immediately 3' to the alternate first exon (encoding the "D" transcript) to a Hind III site approximately 7 kb 3' of this site.

The second DIA gene targeting vector designated DIA IRESβgeo pA was generated by inserting the SV40 polyadenylation sequence immediately 3' to the IRESβgeo transgene. This was accomplished by inserting a Bam HI neo/pA fragment from IRES-βgeo(for targeting) into Bam HI digested 7 kb DIA IRESβgeo. The resultant construct was identical to the 7 kb DIA IRESβgeo targeting construct except for the inclusion of the SV40 polyadenylation signal in place of approximately 400 bp of DIA gene 3' UTR sequence.

The "POS" DIA IRESβgeo targeting vector was generated by inserting a 1400 bp Nco I/Pst I pSVTKNeob fragment, incorporating the rabbit β-globin gene splice acceptor and exon sequences and the SV40 polyadenylation signal, into the Sac II site at the 5' extremity of the DIA gene DNA homology (FIG. 3).

Figure 6:
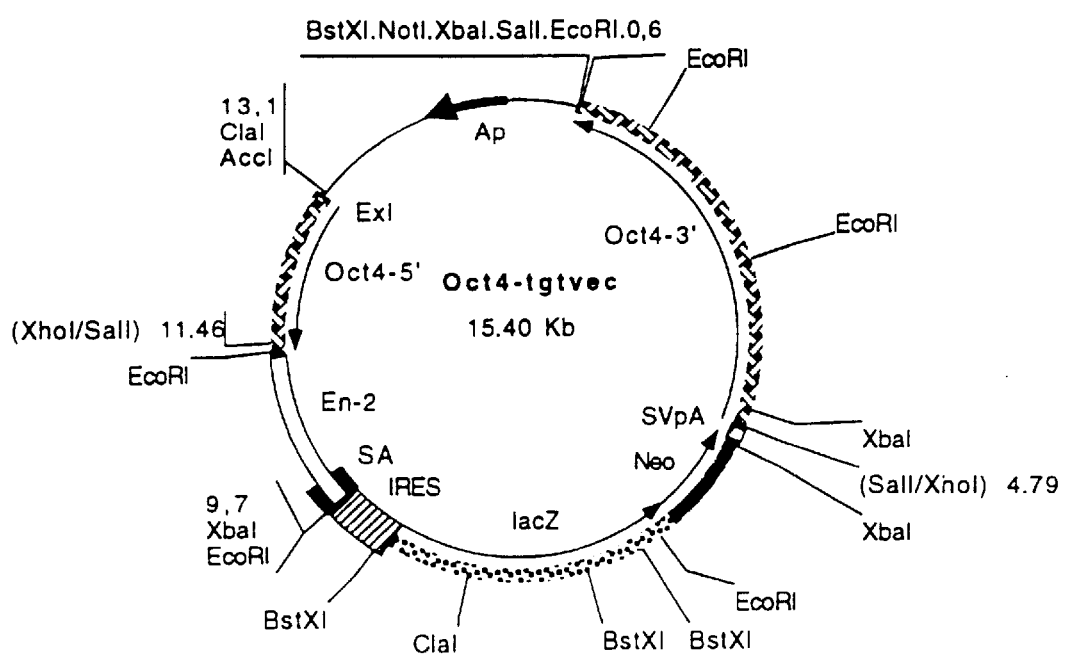

The Oct4-neo construct (Oct4-tgtvec) designed for targeted integration into the Oct4 gene is shown in FIG. 6. This construct incorporates 1.6 kb of 5' Oct4 gene sequence, 4.3 kb of 3' Oct4 gene sequence a lacZ-neomycin fusion gene (βgeo, encoding a bifunctional protein, Freidrich and Soriano, 1991) into the first intron of the Oct4 mRNA. Splicing from the splice donor sequence of the first exon-intron boundary to the integrated IRES-βgeo sequence is facilitated by the inclusion a murine engrailed-2 splice acceptor sequence (Skarnes et al., 1992) immediately 5' to the IRES-βgeo sequence. Translation of the βgeo cistron of the Oct4-βgeo fusion transcript is facilitated by the inclusion of the EMCV-IRES immediately 5' to the βgeo coding sequence.

ES cell transfection and colony selection

Mouse 129 ES cells (line CGR-8) were prepared and maintained in the presence DIA as described by Smith (1991). Plasmid DNA for transfection was linearised by Sal I digest, ethanol precipitated and resuspended at 10–14 mg/ml in PBS. Following 10 hours culture in fresh medium, near confluent ES cells were dispersed by trypsinisation, washed sequentially in culture medium and PBS, and resuspended at $1.4 \times 10^8$/ml in PBS for immediate transfection. Routinely, 0.7 ml of cell suspension was mixed with 0.1 ml DNA containing solution and electroporated at 0.8 kV and 3.0 μFD using a Biorad Gene Pulser and 0.4 cm cuvettes. Transfections were plated on gelatinised tissue culture dishes at $5-8 \times 10^4$/cm² in growth medium for 16 hours prior to the addition of selection medium containing 200 μg/ml (active) G418 (Sigma). Single colonies were picked 8–10 days post transfection and transferred in duplicate into 24 well tissue culture plates for further expansion in growth medium containing 200 μg/ml G418.

Once confluent, one series of cells were frozen for storage while the remainder were analyzed by Southern analysis and/or lacZ staining.

Further characterisation of the DIA gene-targeted cell lines

Selected cell lines were assayed for lacZ staining patterns following ES cell growth and differentiation in DIA-supplemented medium, or following retinoic acid induced differentiation in non-DIA-supplemented medium.

Production of chimaeras from the DIA gene-targeted cell lines

Selected cell lines were cultured in the absence of G418 for 7 days prior to embryo injection as previously described (Nichols et al., 1990). Briefly, blastocysts for injection were collected 4 d.p.c. from C57/B16 donors, injected with 10–20 cells and allowed to re-expand in culture prior to transfer to the uteri of pseudopregnant recipients. Chimaeras were identified by the presence of patches of sandy coat colour on the C57/BL6 background. Male chimaeras may be test bred for transmission of the transgenes. Transgenic mice may be analyzed for lacZ staining.

DNA and RNA Hybridisation Analyses

Filter hybridisations were performed on nylon membranes according to standard procedures using random-primed $^{32}$P-labelled probes. Homologous recombinants were characterised with probes from both 5' and 3' flanking sequences. Whole mount in situ hybridisation with digoxigenin-labelled Oct-4 antisense RNA (Schöler, H., Dressler, G. R., Balling, R., Rohdewold, H. & Gruss, P. (1990) EMBO J. 9, 2185–2195) was performed essentially as described (Wilkinson, D. G. (1992) in situ hybridization: a practical approach, ed. Wilkinson, D. G. (IRL Press, Oxford), pp. 75–83).

The steady state level of DIA/LIF mRNA in ES cells is fewer than 10 copies per cell; this provided a stern test of the general utility of IRES targeting vectors of the invention. Targeting vectors were constructed by introduction of the IRES-βgeo module at the Xba I site which overlaps the stop codon (FIG. 9). The entire coding sequence was thus left intact and intron sequences were unaltered. Two constructs were built, DIA-βgeo and DIA-βgeopA, which differed by inclusion of the SV40 polyadenylation signal 3' of the βgeo sequence. The fusion transcript generated following homologous recombination with the former construct utilises the endogenous 3' UTR and polyadenylation signal of the DIA/LIF gene, whereas the DIA-βgeopA construct gives rise to a truncated transcript lacking these sequences.

In contrast to DIA/LIF, both mRNA and protein for the octamer-binding transcription factor Oct-4 (also known as Oct-3), are relatively abundant in ES cells. Oct-4 is also found in oocytes, pluripotential early embryo cells and primordial germ cells. The association of Oct-4 with pluripotency is strengthened by its rapid down-regulation during differentiation. An IRES-βgeo vector was designed both to generate a null allele and to introduce an expression marker into the Oct-4 locus (FIG. 8). The latter could facilitate the detection of hitherto unidentified sites of Oct-4 expression. The POU-specific domain and the homeodomain coding sequences in exons 2 to 5 were deleted and replaced by the IRES-βgeopA module (FIG. 11). Since the 5' arm of homology ended within the first intron, the en-2 splice acceptor sequence was included 5' to the IRES in order to facilitate productive splicing from exon 1 after homologous recombination.

Following electroporation and selection in G418, individual clones were analyzed by Southern hybridisation with both 5' and 3' flanking probes to detect replacement targeting events (FIG. 9–12) and with internal probes to monitor for multiple integrations. The frequencies of homologous recombination obtained with the constructs of the invention are presented in Table 1.

Correct replacement events were observed with all vectors. A particularly high frequency was reproducibly obtained at the Oct-4 locus. This may reflect the high expression level of this gene in ES cells in addition to the contributions of isogenic DNA and the enrichment afforded by a promoterless construct. Targeting of DIA/LIF with the poly(A) addition vector was also efficient. The isolation of correctly targetted clones at the DIA/LIF locus establishes that IRES-mediated translation is applicable to genes expressed at very low levels in ES cells.

Northern analyses of several targetted clones confirmed that all contained fusion transcripts of the predicted sizes (FIGS. 11,12) which hybridised to both lac Z and DIA/LIF or Oct-4 probes respectively. The transcript generated by nontruncating insertion of IRES-βgeo into the DIA/LIF gene in clone D70 was detected in similar, although slightly lower, amounts to the normal transcript. This indicates that the IRES-βgeo sequence itself does not have any profound influence on either transcription or message turnover. The truncated fusion species produced upon integration of IRES-βgeopA was 5-fold more abundant by phosphorimage scanning than the normal message. The increased level of fusion transcript in these cells was reflected in the production of biologically active DIA/LIF protein; 3–6-fold more DIA/LIF was present in conditioned medium prepared from differentiated cultures of cells with targetted truncations than from the parental cells or cells targetted with the nontruncating construct. Thus the fusion transcript is a functional dicistronic mRNA and the targeting event has modified the activity of the targeted gene. The Oct-4 fusion transcript on the other hand was 10–20-fold less abundant than wild-type Oct-4 mRNA. This could be attributable to inefficient utilisation of the en-2 splice acceptor, but might also arise from deletion of either stabilising elements within the mRNA or an enhancer within the gene.

The in vitro studies illustrate the potential of the constructs and methods of the invention for obtaining targeted heterologous gene expression.

EXAMPLE 2

To address the issue of tissue-specificity of IRES function we made a series of random IRES gene traps according to the invention by electroporation of pGTIRESβgeopA into ES cells. Several clones which exhibited widespread expression of β-galactosidase in differentiated cell types in vitro were used to produce aggregation chimaeras. At 7.5 and 8.5 days of development, β-galactosidase could be detected in all tissues colonised by the ES cells, that is throughout the embryo and in the amnion and visceral yolk sac. These gene traps have been transmitted through the germ line, confirming that the presence of the IRES is compatible with functional gametogenesis, and preliminary analyses on the heterozygotes indicate that the IRES is functional in a wide variety of embryonic and adult tissues. Aggregation chimaeras have also been produced with the Oct-4 targetted cells. The staining pattern of such embryos at 7.5 days shows that the tissue-specific distribution of Oct-4 mRNA is accurately reflected by the β-galactosidase expression pattern.

EXAMPLE 3

Application of the invention to the efficient expression of heterologous molecules by insertion of an IRES and a cDNA into the 3' untranslated region of a genomic clone of a tissue-specific gene and the generation of transgenic animals by microinjection into fertilised eggs.

In the following example a cDNA (eg. human alpha-1 antitrypsin) is inserted, downstream of an IRES (eg. from EMCV), into the 3' untranslated region of a genomic gene that functions efficently and in a tissue-specific manner in transgenic animals (eg. the ovine beta-lactoglobulin gene, BLG).

Figure 13:
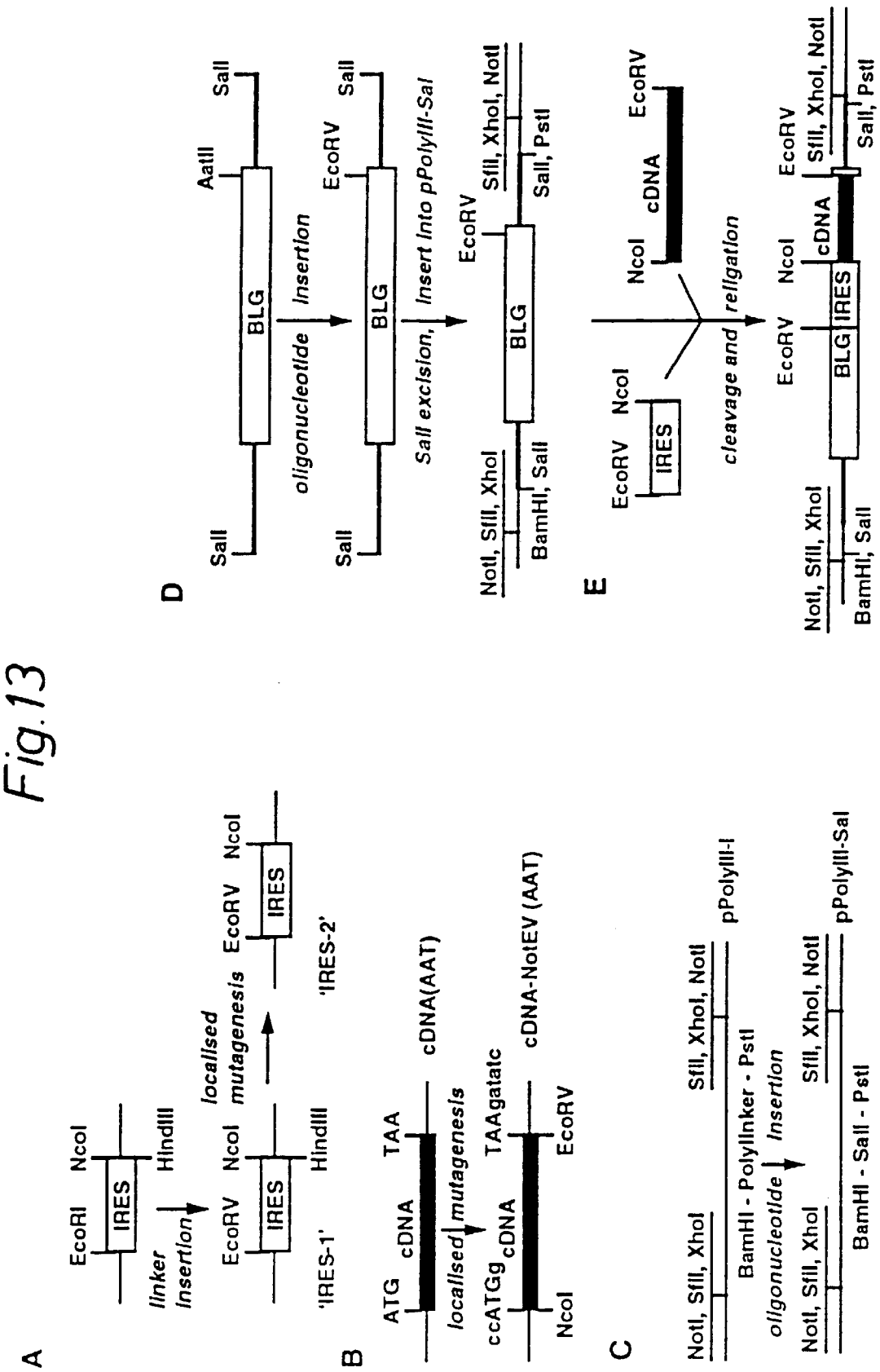

The IRES from encephalomyocarditis virus (EMCV) is available as a 600 bp EcoRI-NcoI fragment, where the NcoI site (CC<u>ATG</u>G) SEQ ID NO: 2 defines the start site of translation; it also contains a HindIII site introduced some nucleotides upstream of the NcoI site, changing the spacing between the IRES and the ATG (Ghattas et al., Mol. Cell. Biol. 11, 5848–5859, 1991). First, the upstream EcoRI site is converted, by linker insertion (sequence GAATT<u>GATATC</u>AATT) SEQ ID NO: 2 to an EcoRV site. Two versions of the IRES are employed, one (IRES-1) in which the heterologous coding sequence is introduced at the NcoI site, a second in which site-directed mutagenesis is used to position the ATG within the NcoI site 20 nucleotides downstream of box A (TTTCC SEQ ID NO: 3, Pilipenko et al., Cell 68, 119–131, 1992), removing the HindIII site (the DNA sequence in this region now reading TTTCCTTTGAAAAACACGATAACC<u>ATG</u>G) SEQ ID NO: 4 (FIG. 13, A). The modified IRES is termed IRES-2. IRES-1 and IRES-2 are both used, as EcoRI-NcoI fragments, for the following experiments.

The ovine BLG gene is present on a large SalI-SalI fragment (or, alternatively as a slightly smaller SalI-XbaI fragment) (Simons et al., Nature 328, 530–532, 1987; Ali and Clark, J. Mol. Biol. 199, 415–426, 1988; Harris et al., Nucl. Acids Res. 16, 10379, 1988) cloned into pPolyIII-I (Lathe et al., Gene 57, 193–201, 1987). Both fragments express at high level in lactating mammary gland when introduced into transgenic animals (Simons et al., Nature 328,530–532, 1987).

Immediately downstream of the translation stop codon in the last exon lies a unique AatII site (GACGT/C) SEQ ID NOS: 5 and 6. This site is converted, by insertion of a linker, to an EcoRV site (final sequence GACGT<u>GATATC</u>ACGTC) SEQ ID NO: 7 (FIG. 13, D). Although this construction is based on the use of the entire SalI-SalI fragment, the SalI-XbaI fragment may also be used with appropriate minor modifications to the procedure.

The reporter gene used in this experiment is human alpha-1 antitrypsin cDNA though the procedure can be repeated with any other cDNA. The cDNA is engineered, by localised mutagenesis, such that an NcoI site overlaps the initiating ATG (this may lead to a single base change in the second codon, so changing the nature of the amino acid encoded at this position. Because in most cases this amino acid does not contribute to the mature protein because it is at the beginning of the signal sequence this has no adverse consequences for expression, secretion or activity of the mature protein). Similarly, an EcoRV site is engineered at the 3' terminus of the cDNA such that the 3' untranslated region is removed (sequence at the 3' terminus of the cDNA reading TAAGATATC SEQ ID NO: 8, where the stop codon TAA could be TAA, TAG or TGA) (FIG. 13, B). The NcoI-EcoRV fragment (obtained, where necessary, by partial digestion in cases where internal sites are present) is used in the following experiments.

Next, pPolyIII-I (Lathe et al., Gene 57, 193–201, 1987) is modified such that a synthetic BamHI-SalI-PstI polylinker is inserted between the BamHI and PstI sites (sequence of polylinker—GGATCCGCGTCGACCACTGCAGSEQ ID NO: 9; restriction sites are underlined) (FIG. 13, C). The SalI-SalI fragment encompassing the modified (EcoRV site at the place of the AatII site) genomic ovine BLG gene is cloned into the SalI site. The IRES and the modified cDNA are excised as EcoRV-NcoI and NcoI-EcoRV fragments respectively, ligated together, and the fusion product EcoRV-NcoI-EcoRV inserted into the EcoRV site within 3' untranslated region of the BLG gene (FIG. 13, E).

The hybrid molecule, BLG-IRES-AAT-BLG, is exercised from the plasmid with SfiI or another appropriate enzyme and microinjected into fertilised eggs of mouse or sheep. Transgenic animals harbouring this construct, for the most part, are observed to express high levels of AAT in their milk. Constructs of the invention could also be used to obtain expression of other proteins of biomedical importance.

The experiments reported here establish that the use of IRES-targeting according to the invention is a powerful means of expressing a desired gene in a host genome. Moreover, the IRES configuration used in these studies was not optimal for translation of the 3' cistron. It has been found that the precise location of the ATG relative to the 3' end of the IRES has a major effect on translational efficiency. It appears that production of βgeo could be increased severalfold over that achieved in the present study. This should increase the ability to isolate recombinants in poorly expressed genes and enhance the sensitivity of the lac Z reporter.

The IRES-targetting strategy of the invention is a powerful means of reporting and modifying mammalian gene expression. Furthermore, it is apparent that non-disruptive integration of an IRES-linked marker into a 3' UTR provides a convenient means for introducing subtle mutations into a gene. Moreover, the IRES strategy is not limited to modification of endogeneous genes and the introduction of reporters, but is also applicable to the controlled expression of transgenes. The desired specificity and levels of transgene expression could be ensured by the use of IRES-mediated translation either in genomic constructs for pronuclear injection or following homologous integration into an appropriate locus. The latter could be achieved by the construction of polycistronic vectors containing two IRES elements. Alternatively, sequential rounds of homologous replacement or targetting followed by recombinational deletion of the selectable marker could be employed to introduce an IRES expression cassette with minimal disruption into any genes which are not expressed in ES cells. In general therefore, the flexibility and utility of IRES-mediated translation seem likely to find widespread application in transgenic research.

TABLE 1

Frequency of Isolation of Homologous Recombinants with IRES vectors.

| Construct | Cell Line | Colonies Screened | Number Positive | Percent Positive |
|---|---|---|---|---|
| Oct4-βgeo | CGR8 | 51 | 44 | 86% |
| Oct4-βgeo | E14TG2a | 10 | 7 | 70% |
| Oct4-βgeo | D1C2 | 30 | 21 | 70% |
| DIA-βgeopA | CGR8 | 79 | 21 | 26% |
| DIA-βgeo | CGR8 | 109 | 3 | 2.7% |
| "POS" DIA-Bgeo | CGR8 | 20 | 20 | 100% |

We claim:

1. A method of inserting a gene coding sequence into a target endogenous gene in a eukaryotic cellular host cell genome and expressing said gene coding sequence, by transforming the host cell with a vector comprising a DNA construct, wherein the host cell is a mouse embryonic stem cell and the DNA construct comprises the elements:

5'X-A-P-B-Q-C-Y3' in which

X and Y are substantially homologous with separate sequences from the target endogenous gene and are of sufficient length to undergo homologous recombination with the host cell genome so as to insert the A-P-B-Q-C elements into the host cell genome;

P is an internal ribosome entry site (IRES);

Q is the gene coding sequence; and

A, B and C are, separately, linker sequences or a covalent bond.

2. The method of claim 1 in which the construct is adapted to insert the gene coding sequence into or in place of the target endogenous gene so that transcription of the gene coding sequence is directed by host regulatory elements for the target endogenous gene.

3. The method of claim 1 in which the construct is adapted to insert the A-P-B-Q-C elements into position 3' (downstream) to the stop codon of an endogenous gene and 5' (upstream) to the polyadenylation signal of the endogenous gene.

4. The method of claim 1 using a construct in which X and Y are each at least 1000 base pairs in length.

5. The method of claim 4 using a construct in which X and Y comprise host elements regulating expression of the target endogenous gene.

6. The method of claim 1 in which the construct additionally comprises a polyadenylation signal at the 3' (downstream) end of the gene coding sequence.

7. The method of claim 1 in which the construct additionally comprises a splice acceptor 5' (upstream) of the IRES.

8. The method of claim 7 in which the splice acceptor is the rabbit β-globin splice acceptor.

9. The method of claim 1 further comprising identifying cells expressing the gene coding sequence.

10. The method of claim 9 in which the gene coding sequence also codes for a selectable marker and the method comprises selecting cells that express the selectable marker.

11. The method of claim 10 in which the selectable marker is a polypeptide that confers antibiotic resistance.

12. A mouse embryonic stem cell comprising an inserted gene coding sequence, wherein the gene coding sequence has been inserted according to the method of claim 1.

13. A descendant of a cell according to claim 12, wherein the descendant has inherited the inserted gene coding sequence.

14. A method of inserting a gene coding sequence into a eukaryotic, cellular host cell genome and expressing said coding sequence under control of elements regulating expression of an endogenous gene in a donor cell genome, said donor cell being a different cell from said host cell, by allowing a DNA construct to undergo random integration into the host cell genome, wherein the host cell is a mouse embryonic stem cell and the DNA construct comprises the sequence:

5'X-A-P-B-Q-C-Y3' in which
- X and Y are homologous with separate sequences from the same donor cell genome and comprise the elements regulating expression of the endogenous gene in the donor cell;
- P is an internal ribosome entry site (IRES);
- Q is the gene coding sequence; and
- A, B and C are, separately, linker sequences or a covalent bond.

15. The method of claim 14 in which the construct additionally comprises a polyadenylation signal at the 3' (downstream) end of the heterologous gene coding sequence.

16. The method of claim 14 in which the construct additionally comprises a splice acceptor 5' (upstream) of the IRES.

17. The method of claim 14 further comprising identifying cells expressing the gene coding sequence.

18. The method of claim 17 in which the gene coding sequence also codes for a selectable marker and the method comprises selecting cells that express the selectable marker.

19. The method of claim 18 in which the selectable marker is a polypeptide that confers antibiotic resistance.

20. A method of inserting a gene coding sequence into a mouse embryonic stem cell genome comprising the steps of:
   (i) randomly integrating a DNA construct into a genome using the method of claim 14; followed by
   (ii) homologously recombining a DNA construct into the genome using the method of claim 1.

21. A mouse embryonic stem cell comprising an inserted gene coding sequence, wherein the gene coding sequence has been inserted according to the method of claim 14.

22. A descendant of a cell according to claim 21, wherein the descendant has inherited the inserted gene coding sequence.

23. A method for inserting a gene coding sequence into a target endogenous gene in a eukaryotic cellular host cell genome and expressing said gene coding sequence in vitro, by transforming the host cell with a vector comprising a DNA construct, wherein the host cell is an animal stem cell and the DNA construct comprises the element:

5'X-A-P-B-Q-C-Y3' in which
- X and Y are homologous with separate sequences from the same donor cell genome and comprise the elements regulating expression of the endogenous gene in the donor cell;
- P is an internal ribosome entry site (IRES);
- Q is the gene coding sequence; and
- A, B and C are, separately, linker sequences or a covalent bond.

24. A method for inserting a gene coding sequence into a eukaryotic, cellular host cell genome and expressing said coding sequence in vitro under control of elements regulating expression of an endogenous gene in a donor cell genome, said donor cell being a different cell from said host cell, by allowing a DNA construct to undergo random integration into the host cell genome, wherein the host cell is an animal stem cell and the DNA construct comprises the sequence:

5'X-A-P-B-Q-C-Y3' in which
- X and Y are homologous with separate sequences from the same donor cell genome and comprise the elements regulating expression of the endogenous gene in the donor cell;
- P is an internal ribosome entry site (IRES);
- Q is the gene coding sequence; and
- A, B and C are, separately, linker sequences or a covalent bond.

25. A method of inserting a gene coding sequence into a target endogenous gene in a eukaryotic cellular host cell genome and expressing said gene coding sequence, by transforming the host cell with a vector comprising a DNA construct, wherein the host cell is a fertilized non-human egg and the DNA construct comprises the elements:

5'X-A-P-B-Q-C-Y3' in which
- X and Y are substantially homologous with separate sequences from the target endogenous gene and are of sufficient length to undergo homologous recombination with the host cell genome so as to insert the A-P-B-Q-C elements into the host cell genome;
- P is an internal ribosome entry site (IRES);
- Q is the gene coding sequence; and
- A, B and C are, separately, linker sequences or a covalent bond.

26. The method according to claim 23 or 25 in which the construct is adapted to insert the A-P-B-Q-C elements into position 3' (downstream) to the stop codon of an endogenous gene and 5' (upstream) to the polyadenylation signal of the endogenous gene.

27. The method according to any one of claims 23 to 25 in which the gene coding sequence also codes for a selectable marker and the method comprises selecting cells that express the selectable marker.

28. The method according to any one of claims 23 to 25 in which the selectable marker is a polypeptide that confers antibiotic resistance.

29. A method of inserting a gene coding sequence into a eukaryotic, cellular host cell genome and expressing said coding sequence under control of elements regulating expression of an endogenous gene in a donor cell genome, said donor cell being a different cell from said host cell, by allowing a DNA construct to undergo random integration into the host cell genome, wherein the host cell is a fertilized non-human egg and the DNA construct comprises the sequence:

5'X-A-P-B-Q-C-Y3' in which
- X and Y are homologous with separate sequences from the same donor cell genome and comprise the elements regulating expression of the endogenous gene in the donor cell;
- P is an internal ribosome entry site (IRES);
- Q is the gene coding sequence; and
- A, B and C are, separately, linker sequences or a covalent bond.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 6 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:1:

CCATGG                                                                      6

(2) INFORMATION FOR SEQ ID NO:2:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

GAATTGATAT CAATT                                                15

(2) INFORMATION FOR SEQ ID NO:3:

(i) SEQUENCE CHARACTERISTICS:
        (A) LENGTH: 5 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

TTTCC                                                                     5

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

TTTCCTTTGA AAAACACGAT AACCATGG                              28

(2) INFORMATION FOR SEQ ID NO:5:

(i) SEQUENCE CHARACTERISTICS:
        (A) LENGTH: 5 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

GACGT                                                                     5

(2) INFORMATION FOR SEQ ID NO:6:

(i) SEQUENCE CHARACTERISTICS:
        (A) LENGTH: 5 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

GACGC                                                                     5

(2) INFORMATION FOR SEQ ID NO:7:

(i) SEQUENCE CHARACTERISTICS:

-continued

```
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

GACGTGATAT CACGTC                                                  16

(2) INFORMATION FOR SEQ ID NO:8:

(i) SEQUENCE CHARACTERISTICS:
        (A) LENGTH: 9 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

TAAGATATC                                                           9

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

GGATCCGCGT CGACCACTGC AG                                           22
```